US009606045B2

(12) United States Patent
Stevens

(10) Patent No.: US 9,606,045 B2
(45) Date of Patent: Mar. 28, 2017

(54) PROGRESSIVE MOISTURE DETECTION

(71) Applicant: HzO, Inc., Draper, UT (US)

(72) Inventor: Blake Stevens, Morristown, NJ (US)

(73) Assignee: HZO, Inc., Draper, UT (US)

( * ) Notice: Subject to any disclaimer, the term of this patent is extended or adjusted under 35 U.S.C. 154(b) by 271 days.

(21) Appl. No.: 14/213,175

(22) Filed: Mar. 14, 2014

(65) Prior Publication Data

US 2014/0260571 A1 Sep. 18, 2014

Related U.S. Application Data

(60) Provisional application No. 61/800,178, filed on Mar. 15, 2013.

(51) Int. Cl.

| | |
|---|---|
| ***G01N 19/10*** | (2006.01) |
| ***G01D 7/00*** | (2006.01) |
| ***G01N 21/81*** | (2006.01) |
| ***G01N 31/22*** | (2006.01) |

(52) U.S. Cl.

CPC ............. *G01N 19/10* (2013.01); *G01D 7/005* (2013.01); *G01N 21/81* (2013.01); *G01N 31/222* (2013.01)

(58) Field of Classification Search

CPC ...... G01D 7/005; G01N 31/222; G01N 19/10; G01N 21/81

See application file for complete search history.

(56) References Cited

U.S. PATENT DOCUMENTS

| | | | | |
|---|---|---|---|---|
| 5,868,723 | A | 2/1999 | Al-Sabah | |
| 2003/0217585 | A1* | 11/2003 | Duncan | G01N 19/10 73/29.01 |
| 2005/0078557 | A1* | 4/2005 | Andersen | G01N 21/81 368/11 |
| 2010/0304091 | A1 | 12/2010 | Wang | |
| 2011/0011179 | A1 | 1/2011 | Gustafsson et al. | |
| 2012/0137959 | A1 | 6/2012 | Kwak | |

OTHER PUBLICATIONS

United States Patent and Trademark Office Acting as the International Searching Authority, "International Search Report and Written Opinion," mailed Aug. 19, 2014 in related international application No. PCT/US2014/029443.

* cited by examiner

*Primary Examiner* — Paul West
(74) *Attorney, Agent, or Firm* — Kunzler Law Group

(57) ABSTRACT

A progressive, or graded, passive moisture detector is configured to provide an indication of the amount of moisture to which a moisture-sensitive substrate has been exposed, a duration of time that a moisture-sensitive substrate has been exposed to moisture or the effectiveness of one or more protective coatings at preventing moisture-sensitive components from being exposed to moisture. A progressive passive moisture detector includes a plurality of different passive moisture detectors with different properties. The passive moisture detectors may be arranged in a manner (e.g., a sequence, etc.) that correlates to information the progressive passive moisture detector is intended to provide.

23 Claims, 1 Drawing Sheet

200

210

212

100

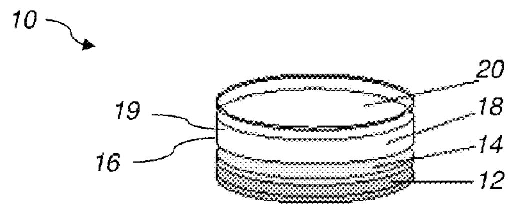
FIG. 1
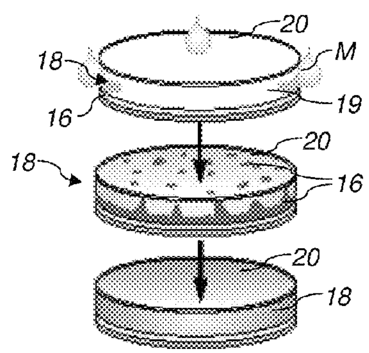
FIG. 2
FIG. 3A
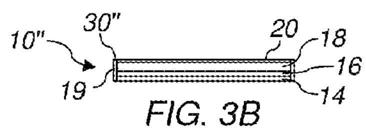
FIG. 3B
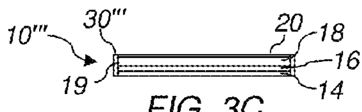
FIG. 3C
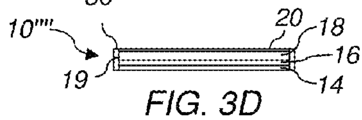
FIG. 3D
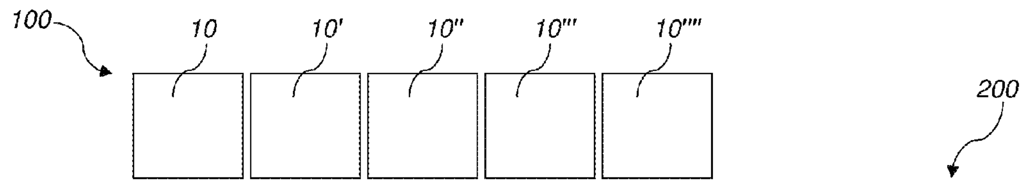
FIG. 4
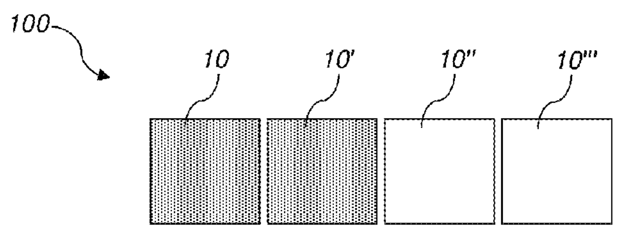
FIG. 5
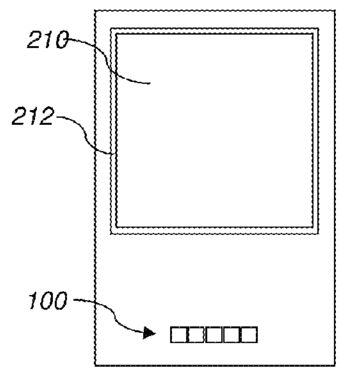
FIG. 6

PROGRESSIVE MOISTURE DETECTION

CROSS-REFERENCE TO RELATED APPLICATION

A claim is hereby made, pursuant to 35 U.S.C. §119(e), for the benefit of priority to the Mar. 15, 2013 filing date of U.S. Provisional Patent Application No. 61/800,178, titled "PROGRESSIVE MOISTURE DETECTION," the entire disclosure of which is hereby incorporated herein.

TECHNICAL FIELD

This disclosure relates generally to passive moisture detectors and, more specifically, to progressive, or graded, passive moisture detectors that are configured to provide an indication of the amount of moisture exposure and/or the duration of moisture exposure. This disclosure also relates to electronic devices or other substrates with graded moisture detectors, including electronic devices or other substrates with moisture-resistant coatings.

RELATED ART

Passive moisture detectors are referred to in the art by a variety of names, including, without limitation, as liquid submersion indicators (LSIs), water contact indicators, water damage indicators, liquid contact indicators (LCIs) and moisture detecting stickers. Typically, a passive moisture detector 10, an embodiment of which is depicted by FIG. 1, has a laminate construction, including, from bottom to top, a release liner 12, an adhesive layer 14, dye 16, an indicator layer 18 and a transparent film 20. The release liner 12 is configured to be removed from and, thus, to expose the adhesive layer 14 just before securing the passive moisture detector 10 to a substrate (not shown). The adhesive layer 14 is configured to secure the passive moisture detector 10 to a substrate. The dye 16 may be located beneath the indicator layer 18, or it may be dispersed throughout at least a portion of the indicator layer 18. The indicator layer 18 comprises a wicking material, and is typically white in color or includes white areas. The transparent film 20 enables detection of any change in the color of the indicator layer 18. Although the transparent film 20 covers the top of the indicator layer 18, the peripheral edges 19 of the indicator layer 18 are exposed.

When the peripheral edges 19 of the indicator layer 18 are exposed to water, the dye 16 may be activated. In embodiments where the dye 16 is located beneath the indicator layer 18, activation of the dye 16 may simply comprise dissolving of the dye 16 by the moisture, which then enables the dye 16 to wick, or pass by capillary action, or otherwise permeate into and throughout the indicator layer 18, where the dye 16 and its effect on the indicator layer 18 (e.g., a change in color) will be visible through the transparent film 20. Dye 16 that is pre-dispersed throughout the indicator layer 18 may be configured to change color upon exposure to water, as will occur when moisture contacts a peripheral edge 19 of the indicator layer 18 and wicks into the indicator layer 18.

FIG. 2 illustrates an example of how dye 16 changes the color of the indicator layer 18 of a passive moisture detector 10 when the indicator layer 18 is exposed to moisture M (e.g., water (including condensation), alcohol and liquids that include water or alcohol, etc.). Typically, only a very small amount of liquid moisture M (e.g., a drop or less, etc.) is required to wet the indicator layer 18 and cause the dye 16 to change color and/or permeate into the indicator layer 18 of a passive moisture detector 10 that has been installed in an electronic device. The color change in the indicator layer 18 of a conventional passive moisture detector 10 will typically occur in a minute or less, and is irreversible. The indicator layers 18 of passive moisture detectors 10 are often white prior to being exposed to liquid moisture, and then turn pink or red when exposed to liquid moisture.

Manufacturers of electronic devices typically install passive moisture detectors 10 in electronic devices at one or more locations. The use of passive moisture detectors 10 is particularly appealing with electronic devices because passive moisture detectors 10 work even if the electronic device with which they are used is turned off or has quit working. In mobile telephones with removable battery covers, passive moisture detectors 10 can often be found in the battery compartment. In addition, many electronic device manufacturers place passive moisture detectors at less accessible locations within the interiors of electronic devices (e.g., on or near the charging circuit, on the main board, etc., in many portable electronic devices), including locations that, if accessed by a consumer, would void any manufacturer's warranty that covers defects in the electronic device.

The primary purpose of passive moisture detectors 10 in consumer electronic devices has been to enable manufacturers to determine whether an electronic device has been exposed to liquid moisture and, if so, to provide a warranty provider with some indication that a warranty-voiding event has occurred. Passive moisture detectors 10 also enable insurance companies and repair/refurbish/rebuild facilities to determine the likely cause(s) of damage to an electronic device. Passive moisture detectors 10 may also be informative to consumers.

As noted above, the indicator layers 18 of passive moisture detectors 10 that are commonly used in consumer electronic devices change color when exposed to even very small amounts of liquid moisture M—a feature that may be beneficial to manufacturers or other warranty providers, but often to the detriment of consumers.

SUMMARY

A progressive moisture detector, which is also referred to as a "progressive passive moisture detector," includes a plurality of areas or sections that have different sensitivities to moisture. Such a progressive moisture detector may be configured to provide an indication of an amount, duration, or even a type of moisture to which the progressive moisture detector, as well as the water-sensitive substrate (e.g., an electronic device, etc.) with which the progressive moisture detector has been associated, have been exposed.

The term "moisture" refers water, an aqueous solution (e.g., salt solutions, acidic solutions, basic solutions, drinks, etc.) or vapors of water or other aqueous materials (e.g., humidity, fogs, mists, wetness, etc.). The term "moisture" may also refer to organic liquids or vapors (e.g., organic solvents, other organic materials in liquid or vapor form, etc.), as well as a variety of other substances or conditions that might pose a threat to a substrate, such as an electronic device or its components.

In one aspect, a progressive moisture detector according to this disclosure is configured to progressively change color (e.g., along its length, along a circular path, etc.) (to the same color or different colors) depending upon the amount of moisture the progressive moisture detector is exposed to, the duration of exposure to moisture and/or the type of moisture to which the progressive moisture detector is exposed (e.g., does it have a particular (threshold) salt content? does it have a particular (threshold) sugar content? is it carbonated? did it come from the toilet? etc.).

In a specific embodiment, a progressive moisture detector may include a series of physically discrete passive moisture detectors that are configured to change color at different points in time from one another based on different thresholds. As an example, a first passive moisture detector in a series that defines a progressive moisture detector may comprise a conventional passive moisture detector, which changes color upon being exposed to moisture, while each successive passive moisture detector in the series may be configured to change color when exposed to moisture for a particular period of time or range of periods of time, with each successive passive moisture detector being configured to maintain its original color for a progressively longer period or range of periods of time.

A progressive indication of moisture exposure may be accomplished in a variety of ways. Without limitation, the periphery of a first passive moisture detector in the series may comprise a conventional passive moisture detector that lacks any coating on the peripheral edges of its indicator layer (and which may undergo a color change when exposed to moisture for about a minute or less), while each successive passive moisture detector in the series may be coated with material(s) that inhibit moisture from contacting the indicator layer for progressively increasing periods of time (e.g., about fifteen minutes, about thirty minutes, about forty-five minutes, about sixty minutes, any other suitable time increment, etc.).

In a specific embodiment, a plurality of different types of moisture-resistant materials may be coated onto the peripheral edges of the indicator layers of the various passive moisture detectors of a progressive moisture detector. By way of non-limiting example, the peripheral edges of an indicator layer of a first passive moisture detector in series may remain uncoated, while the peripheral edges of the indicator layers of successive passive moisture detectors in the series may be coated with progressively increasing thicknesses of a moisture-resistant coating on one or more components or other features of an electronic device or other moisture-sensitive substrate, with the thickness of the moisture-resistant coating on the peripheral edges of the indicator layer of the last passive moisture detector in the series being the same as or substantially the same as the thickness (or average thickness) of the moisture-resistant coating that covers portions of the electronic device or other moisture-sensitive substrate.

In another specific embodiment, different types of coatings may be applied to the peripheral edges of the indicator layers of the passive moisture detectors of a progressive moisture detector. Without limitation, in series, the peripheral edges of an indicator layer of a first passive moisture detector may remain exposed, while a water repellant coating may be applied to the peripheral edges of the indicator layer of a second passive moisture detector and a water resistant coating may be applied to the peripheral edges of the indicator layer of a third passive moisture detector. Of course, combinations of different materials and different thicknesses may also be employed.

As an alternative to coating peripheral edges of the indicator layer of a conventional passive moisture detector, the various sections of a progressive moisture detector of this disclosure may include indicator layers that transport liquid moisture at different rates from one another (e.g., with different pore sizes, different interstitial spacing, etc.). As another option, dyes that react to one or more types of moisture differently from one another (e.g., that have different dissolution rates, that react to different types of solutes or other materials present in moisture, etc.) may be included in a progressive moisture detector.

When a progressive moisture detector is used, the level of detection (e.g., the portion of the detector that exhibits a visible change, etc.) may correspond to an amount of moisture exposure to which the detector has been exposed or a duration of exposure of the progressive moisture detector to moisture.

Indicia may be provided on or in conjunction with the passive moisture detectors of a progressive moisture detector to enable an individual viewing the progressive moisture detector to readily comprehend the significance of the lack of a change in appearance or a change in appearance of each passive moisture detector of the progressive moisture detector. In embodiments where the different passive moisture detectors are configured to undergo changes in appearance based on the amount of time each is exposed to moisture, the indicia may communicate the duration of time (or approximate duration of time) of moisture exposure that is or was required to cause the appearance of that passive moisture detector to change. In embodiments where the appearance of each passive moisture detector of a progressive moisture detector changes based on the type of moisture to which that passive moisture detector is exposed, the indicia may correspond to the type or types of moisture that will cause or have caused the change in appearance.

Knowing the amount, duration and/or type of moisture exposure may enable selection of reactive measures. For example, exposure of a device to simple moisture (e.g., without salts, sugars or other ingredients) may indicate that certain measures should be taken to remove moisture from the electronic device or other moisture-sensitive substrate. If the moisture to which an electronic device or other moisture-sensitive substrate was exposed also included salts, remedial instructions may include actions that will remove or counteract the effects of salts on the electronic device or other moisture-sensitive substrate (salts cause corrosion) before drying the device. If an electronic device or other moisture-sensitive substrate is exposed to a sugary or sticky substance, additional measures may be taken to remove that substance from the device before drying the device.

A progressive moisture detector may be associated with a moisture-sensitive substrate, such as an electronic device, after the substrate has been manufactured (e.g., by a reseller, by a party that applies moisture-resistant coatings to devices post-manufacture, by a consumer, etc.) to enable an end-user or another party to readily determine whether the substrate has been exposed to moisture and, optionally, the amount, duration and/or type of moisture to which the substrate has been exposed. In some embodiments, a progressive moisture detector may be assembled with a moisture-sensitive substrate after one or more coatings have been applied to the moisture-sensitive substrate. When a passive moisture detector of a progressive moisture detector includes a coating that is substantially the same as a moisture-resistant coating on a moisture-sensitive substrate, the appearance of that passive moisture detector may provide a reliable indicator of the integrity of the moisture-resistant coating.

Other aspects, as well as features and advantages of various aspects, of the disclosed subject matter will become apparent to those of ordinary skill in the art through consideration of the disclosure, the accompanying drawings and the appended claims.

BRIEF DESCRIPTION OF THE DRAWINGS

In the drawings:

FIG. 1 is a perspective view of an embodiment of a conventional passive moisture detector;

FIG. 2 illustrates an embodiment of how a conventional passive moisture detector works;

FIGS. 3A through 3D depict embodiments of passive moisture detectors with peripheral edges that are covered with coatings having different thicknesses;

FIG. 4 is a schematic representation of an embodiment of progressive moisture detector, which is passively configured to detect moisture and to provide some indication about the moisture;

FIG. 5 illustrates an embodiment of the manner in which a progressive moisture detector may respond to moisture over time; and FIG. 6 is a schematic representation of a moisture-sensitive substrate with a passive moisture detector and at least one component at least partially covered with a protective coating.

DETAILED DESCRIPTION

FIGS. 1 and 2 illustrate an embodiment of a passive moisture detector 10, as well as the effect of moisture exposure on the passive moisture detector 10.

In FIGS. 3A through 3D, embodiments of passive moisture detectors 10', 10", 10'", 10"" with sealed indicator layers 18 are shown. More specifically, each of FIGS. 3A through 3D depicts an embodiment of passive moisture detector 10', 10", 10'", 10"" with an indicator layer 18. A dye 16 is associated with each layer 18 in such a way that, when moisture M (FIG. 2) impinges upon and wets the indicator layer 18, the dye 16 will also be wetted, resulting in a change in the color of the passive moisture detector 10', 10", 10'", 10"", such as a change in the color of the dye 16, a change in the color of the indicator layer 18 or both.

Each passive moisture detector 10', 10", 10'", 10"" also includes a peripheral coating 30', 30", 30'", 30"" covering the peripheral edges 19 of its indicator layer 18. As is evident when FIGS. 3A through 3D are viewed together, in some embodiments, the thickness of each peripheral coating 30', 30", 30'", 30"" may differ, with the thickness of the peripheral coatings 30', 30", 30'", 30"" becoming progressively larger from passive moisture detector 10' to passive moisture detector 10"". In a specific embodiment, each peripheral coating 30', 30", 30'", 30"" may be formed from the same type of material that forms one or more protective coatings (e.g., a moisture-resistant coating, a moisture-repellant coating, etc.) on components of an electronic device or other moisture-sensitive substrate with which the passive moisture detectors 10', 10", 10'", 10"" are to be used. Even more specifically, the peripheral coatings 30', 30", 30'", 30"" may be formed from a poly(p-xylylene), or a parylene. The thickness of the thickest peripheral coating 30"" (FIG. 3D) may be the same as or substantially the same as the thickness of a corresponding protective coating on one or more components of the electronic device or other moisture-sensitive substrate with which the passive moisture detector 10"" is configured to be used. In embodiments where an electronic device or other moisture-sensitive substrate includes a protective layer with a thickness (e.g., an average thickness, a minimum thickness, etc.) of 2 μm to 6 μm (i.e., about 4 μm), the peripheral coating 30"" of passive moisture detector 10"" may also have a thickness of 2 μm to 6 μm (i.e., about 4 μm). In such embodiments, peripheral coating 30'" may have a thickness of about 3 μm, peripheral coating 30" may have a thickness of about 2 μm and peripheral coating 30' may have a thickness of about 1 μm.

In other embodiments, the peripheral coatings 30', 30", 30'" of a group of passive moisture detectors 10', 10", 10'" may be formed from different protective materials. The protective materials from which the peripheral coatings 30', 30", 30'" are formed may correspond to protective materials that are used with an electronic device or other moisture-sensitive substrate with which the group of passive moisture detectors 10', 10", 10'" is to be used. As a non-limiting example, peripheral coating 30' may be formed from a moisture-repellant material, while peripheral coating 30" may be formed from a moisture-resistant material and peripheral coating 30'" may include a moisture-resistant material with a moisture-repellant coating thereon. The peripheral coatings 30', 30", 30'" may be configured substantially the same as or the same as corresponding protective coatings of an electronic device or other moisture-sensitive substrate with which the passive moisture detectors 10', 10", 10'" are to be used.

As another option, the peripheral coatings 30', 30", etc., may be formed from materials that degrade when exposed to moisture, with each peripheral coating 30', 30", etc., degrading at a different rate, and in a different amount of time, than the other peripheral coatings 30', 30", etc. Examples of such materials include gelatin, carrageenans, modified starch, modified cellulose and the like.

As yet another option, the peripheral coatings 30', 30", etc., may comprise water-insoluble materials with pores or other passages that impede the flow of moisture therethrough without totally preventing moisture from flowing therethrough. The pores or other passages through each peripheral coating 30', 30", etc., may correspond to a certain amount of time or a range of times that that peripheral coating 30', 30", etc., will prevent moisture from reaching the indicator layer 18. The pores or other passages through each peripheral coating 30', 30", etc., may differ from the pores or other passages through the other peripheral coatings 30', 30", etc., of a set of passive moisture detectors 10, 10', 10", etc., that makes up a progressive passive moisture detector 100; thus, the time or range of times that the various peripheral coatings 30', 30", etc., of a set of passive moisture detectors 10, 10', 10", etc., will prevent moisture from reaching their respective indicator layers 18 differs from one passive moisture detector 10, 10', 10", etc., to another.

The indicator layer 18 is configured to transport liquids, such as water. Some suitable materials include fibrous materials (e.g., a paper, a polyolefin, etc.), woven materials (e.g., a fabric, a polyolefin, etc.) and porous materials (e.g., a polyolefin, etc.). In some embodiments, the material from which the indicator layer 18 is formed may include or be treated with a material (e.g., a hydrophilic material, etc.) that enhances wicking.

The dye 16 may comprise any suitable, water soluble dye or ink, such as the dyes sold by BASF Corp. of Mount Olive, N.J., as FASTUSOL Red 43LN and BASACID RED NB 391L. Other colors of dyes may also be used.

In addition, each passive moisture detector 10', 10", 10'", 10"" may include a transparent film 20 over a top of the indicator layer 18. The transparent film 20 (e.g., its configuration, the material from which it is formed, etc.) may limit or prevent exposure of an upper surface of the indicator layer 18 to moisture M (FIG. 2), while enabling an individual to see any change in the color of the dye 16 and/or the indicator layer 18. In a specific embodiment, the transparent film 20 may comprise polyethylene terephthalate (PET).

Optionally, a passive moisture detector 10', 10'', 10''', 10'''' may include an adhesive layer 14 adjacent to the indicator layer 18 or a dye 16-carrying layer that has been secured to the indicator layer 18. In embodiments where the passive moisture detector 10', 10'', 10''', 10'''' includes a transparent film 20 on the indicator layer 18, the adhesive layer 14 may be located on an opposite side of the indicator layer 18 from the transparent film 20. Such an adhesive layer 14 may be applied directly to another element of the passive moisture detector 10', 10'', 10''', 10'''' (e.g., the indicator layer 18, a layer that carries dye 16, etc.) or it may be part of a dedicated adhesive-bearing element (e.g., a film with an adhesive layer 14 on both sides thereof, etc.). In specific embodiments, the adhesive layer 14 may comprise an acrylic adhesive.

Turning now to FIG. 4, an embodiment of a progressive passive moisture detector 100 is illustrated. Progressive passive moisture detector 100 includes at least two different passive moisture detectors 10, 10'. In some embodiments, a progressive passive moisture detector 100 may include more than two passive moisture detectors 10, 10', 10''. In the embodiment illustrated by FIG. 4, the progressive passive moisture detector 100 includes five passive moisture detectors 10, 10', 10'', 10''' and 10''''. Regardless of their number, the passive moisture detectors 10, 10', 10'', 10''', 10'''' of a progressive passive moisture detector 100 may be arranged in a manner that provides an indication of the effect of moisture exposure on an electronic device or other moisture-sensitive substrate with which the progressive passive moisture detector 100 is used.

As a non-limiting example, in embodiments where the progressive passive moisture detector 100 includes passive moisture detectors 10', 10'', 10''', 10'''' with peripheral coatings 30', 30'', 30''', 30'''' (FIGS. 3A through 3D) through which water may permeate at different rates, the passive moisture detectors 10, 10', 10'', 10''', 10'''' may be arranged in a manner that provides some indication of the amount of time the progressive passive moisture detector 100 was exposed to moisture. In such an embodiment, as illustrated by FIG. 5, a change in the appearance of a first passive moisture detector 10 may reveal that the progressive passive moisture detector 100 has been exposed to moisture, the first passive moisture detector 10 having undergone a change in appearance shortly after being exposed to moisture (after a short, first duration of time). The change in appearance of a second passive moisture detector 10' without a corresponding change in the appearance of a third passive moisture detector 10'' may indicate that the progressive passive moisture detector 100 has been exposed to moisture for a prolonged duration of time, or for a second duration of time (e.g., fifteen minutes, thirty minutes, etc.), which exceeds the first duration of time. The progressive passive moisture detector 100 has not been exposed to moisture for enough time (i.e., for a third duration of time, which exceeds the second duration of time) to allow the moisture to permeate into the indicator layer 18 (FIG. 3B) of the third passive moisture indicator 10'' (e.g., thirty minutes, sixty minutes, etc., respectively).

As another non-limiting example, in embodiments where the progressive passive moisture detector 100 includes passive moisture detectors 10', 10'', 10''' with peripheral coatings 30', 30'', 30''' (FIGS. 3A through 3C) formed from different materials, such as different protective coatings (e.g., a moisture-repellant coating, a moisture-resistant coating, a moisture-resistant coating coated with a moisture-repellant material, respectively), the passive moisture detectors 10', 10'', 10''' may be arranged in a manner that reveals the effectiveness of corresponding protective coatings on an electronic device or other moisture-sensitive substrate with which the progressive passive moisture detector 100 is used. With reference to FIG. 5, a first passive moisture detector 10, which lacks a peripheral coating, indicates that the progressive passive moisture detector 100 has been exposed to moisture. A second passive moisture detector 10' indicates that its protective coating 30' did not prevent moisture from permeating into its indicator layer 18 (FIG. 3A), but that the protective coatings 30'' and 30''' of a third passive moisture detector 10'' and a fourth passive moisture detector 10''', respectively, prevented moisture from permeating into their respective indicator layers 18. Such information may also indicate which components of an electronic device or other moisture-sensitive substrate have been exposed to moisture and which components of the electronic device or other moisture-sensitive substrate were protected from moisture.

Although FIGS. 3A-5 depict the passive moisture detectors 10, 10', 10'', etc., as being square in shape, other suitable shapes are also within the scope of this disclosure. For example, a passive moisture detector may have a circular, triangular or hexagonal shape, or any other desired polygonal configuration. As another example, a passive moisture detector may be shaped as a sector (i.e., as a pie piece).

As an alternative to arranging passive moisture detectors 10, 10', 10'', etc., sequentially to form a progressive passive moisture detector 100, as shown in FIGS. 4 and 5, the passive moisture detectors 10, 10', 10'', etc., may be arranged in any other suitable configuration. As an example, the passive moisture detectors 10, 10', 10'', etc., may be arranged in a polygonal pattern (e.g., as a triangle, as a square, as a rectangle, as a pentagon, as a hexagon, etc.). As another example, the passive moisture detectors 10, 10', 10'', etc., may be positioned in a circular arrangement, in which the passive moisture detectors 10, 10', 10'', etc., may be arranged in a circle or shaped as sectors that form a circle. In yet another example, passive moisture detectors 10, 10', 10'', etc., may be superimposed, or stacked, relative to one another.

In FIG. 6, an embodiment of a moisture-sensitive substrate 200, such as an electronic device, that includes a progressive passive moisture detector 100 is depicted. The moisture-sensitive substrate 200 includes at least one component 210 that is at least partially covered with a protective coating 212. In some embodiments, the protective coating 212 may be configured to prevent the component 210, as well as other components and/or features associated with the component 210, from being exposed to moisture. Without limitation, the protective coating 212 may comprise a moisture-repellant material and/or a moisture-resistant material. The progressive passive moisture detector 100 may be configured in a manner that corresponds to the protective coating(s) 212 of the moisture-sensitive substrate 200. For example, the progressive passive moisture detector 100 may include one or more passive moisture detectors 10', 10'', 10''', 10'''' (FIGS. 3A through 3F) with a peripheral coating 30', 30'', 30''', 30'''' that corresponds to (e.g., is formed from the same material(s) as, has the same or substantially the same protective properties as (e.g., thickness, resistance, impermeability, etc.)) at least one protective coating 212 of the moisture-sensitive substrate 200. As disclosed previously herein, the progressive passive moisture detector 100 may enable an individual to evaluate whether or not the moisture-sensitive substrate 200 has been exposed to moisture, as well as the potential effects or the actual effects of moisture exposure on the moisture-sensitive substrate 200.

Although the foregoing disclosure provides many specifics, these should not be construed as limiting the scope of any of the ensuing claims. Other embodiments may be devised which do not depart from the scopes of the claims. Features from different embodiments may be employed in combination. The scope of each claim is, therefore, indicated and limited only by its plain language and the full scope of available legal equivalents to its elements.

What is claimed:

1. A progressive moisture detector, comprising:

a plurality of physically discrete, adjacent, but spaced apart moisture detection elements comprising:

a first moisture detection element comprising a first moisture-resistant coating covering a first circumferentially exposed peripheral surface of a first indicator layer exposed between a first bottom layer and a first top film, and a second moisture detection element physically separate from the first moisture detection element comprising a second moisture-resistant coating covering a second circumferentially exposed peripheral surface of a second indicator layer exposed between a second bottom layer and a second top film;

wherein the first moisture-resistant coating is laterally spaced apart from the second moisture-resistant coating and configured to react to a moisture exposure event differently from the second moisture-resistant coating.

2. The progressive moisture detector of claim 1, wherein the plurality of discrete, adjacent, but spaced apart moisture detection elements are arranged in a series that corresponds to a moisture sensitivity of each moisture detection element of the plurality.

3. The progressive moisture detector of claim 2, wherein:

the first moisture detection element in the series is configured to change appearance when exposed to moisture for a first duration of time; and the second moisture detection element in the series is configured to change appearance when exposed to moisture for a second duration of time, the second duration less than the first duration.

4. The progressive moisture detector of claim 3, the plurality of physically discrete, adjacent, but spaced apart moisture detection elements further comprising a third moisture detection element, wherein the third moisture detection element comprises a third circumferentially peripheral, laterally exposed surface of a third indicator layer and wherein the third moisture detection element lacks a moisture-resistant coating covering the third circumferentially peripheral, laterally exposed surface of the third indicator layer that inhibits exposure of an indicator of the first moisture detection element to moisture.

5. The progressive moisture detector of claim 4, wherein the third moisture detection element is configured to change appearance when exposed to moisture for about a minute or less.

6. The progressive moisture detector of claim 4, wherein the second moisture-resistant coating covering the second circumferentially peripheral, laterally exposed surface of the second indicator layer inhibits exposure of an indicator of the second moisture detection element to moisture.

7. The progressive moisture detector of claim 6, wherein:

the third moisture detection element in the series is configured to change appearance when exposed to moisture for a third duration of time, the third duration less than the second duration.

8. The progressive moisture detector of claim 7, wherein the third moisture detection element includes a feature that inhibits exposure of an indicator of the third moisture detection element to moisture.

9. The progressive moisture detector of claim 3, wherein the second moisture-resistant coating of the second moisture detection element and the first moisture-resistant coating of the first moisture detection element comprise coatings formed from the same material, but having different thicknesses.

10. The progressive moisture detector of claim 3, wherein the second moisture-resistant coating of the second moisture detection element and the first moisture-resistant coating of the first moisture detection element are made of different materials.

11. The progressive moisture detector of claim 3, wherein the second moisture-resistant coating of the second moisture detection element and the first moisture-resistant coating of the first moisture detection element have different permeabilities to moisture.

12. The progressive moisture detector of claim 3, wherein the first moisture detection element and the second moisture detection element comprise different dyes that are dissolved by a type of moisture at different rates.

13. An electronic device, comprising:

an electronic device; and a plurality of physically discrete, adjacent, but spaced apart moisture detection elements comprising:

a first moisture detection element comprising a first moisture-resistant coating covering a first circumferentially exposed peripheral surface of a first indicator layer exposed between a first bottom layer and a first top film, and a second moisture detection element physically separate from the first moisture detection element comprising a second moisture-resistant coating covering a second circumferentially exposed peripheral surface of a second indicator layer exposed between a second bottom layer and a second top film;

wherein the first moisture-resistant coating is laterally spaced apart from the second moisture-resistant coating and configured to react to a moisture exposure event differently from the second moisture-resistant coating.

14. The electronic device of claim 13, further comprising:

a moisture-resistant coating on at least a portion of the electronic device.

15. The electronic device of claim 14, wherein the moisture-resistant coating is on at least some surfaces within an interior of the electronic device.

16. The electronic device of claim 14, further comprising a third moisture detection element, wherein the third moisture detection element of the plurality includes laterally exposed surface of a third indicator layer not protected by a moisture-resistant coating.

17. The electronic device of claim 16, wherein the first moisture-resistant coating and the moisture-resistant coating on at least a portion of the electronic device comprise the same material.

18. The electronic device of claim 17, wherein the second moisture-resistant coating comprises a different material from a material of the first moisture-resistant coating.

19. The electronic device of claim 17, wherein the first moisture-resistant coating and the moisture resistant coating on at least a portion of the electronic device have about the same thicknesses.

20. A method for obtaining information about a moisture exposure event, comprising:

viewing a plurality of laterally discrete passive moisture detection sections of the progressive moisture detector providing different visible information about the moisture detection event, the plurality of laterally discrete passive moisture detection sections comprising:

a first moisture detection element comprising a first moisture-resistant coating covering a first circumferentially exposed peripheral surface of a first indicator layer exposed between a first bottom layer and a first top film, and a second moisture detection element physically separate from the first moisture detection element comprising a second moisture-resistant coating covering a second circumferentially exposed peripheral surface of a second indicator layer exposed between a second bottom layer and a second top film;

wherein the first moisture-resistant coating is laterally spaced apart from the second moisture-resistant coating;

determining whether or not an appearance of each passive moisture detection section of the progressive moisture detector has changed; and correlating information about an appearance of each passive moisture detection section to a moisture exposure event.

21. The method of claim 20, wherein correlating comprises considering an indicia on at least one passive moisture detection section.

22. The method of claim 20, wherein correlating comprises determining a duration of the moisture exposure event.

23. The method of claim 22, wherein determining the duration of the moisture exposure event comprises determining a combined duration of a plurality of moisture exposure.

* * * * *